United States Patent
Meyers et al.

(10) Patent No.: US 11,679,146 B2
(45) Date of Patent: Jun. 20, 2023

(54) COMPOSITIONS AND METHODS FOR TREATING PANCREATITIS

(71) Applicant: Anji Pharmaceuticals Inc., Cambridge, MA (US)

(72) Inventors: Charles D. Meyers, Littleton, MA (US); Brian K. Hubbard, Boxford, MA (US); Michael H. Serrano-Wu, Belmont, MA (US)

(73) Assignee: Anji Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 15/734,461

(22) PCT Filed: Jun. 4, 2019

(86) PCT No.: PCT/US2019/035310
§ 371 (c)(1),
(2) Date: Dec. 2, 2020

(87) PCT Pub. No.: WO2019/236528
PCT Pub. Date: Dec. 12, 2019

(65) Prior Publication Data
US 2021/0213111 A1 Jul. 15, 2021

Related U.S. Application Data

(60) Provisional application No. 62/680,896, filed on Jun. 5, 2018.

(51) Int. Cl.
| | | |
|---|---|---|
| *A61K 39/395* | (2006.01) | |
| *A61K 31/7105* | (2006.01) | |
| *A61K 31/712* | (2006.01) | |
| *A61K 38/00* | (2006.01) | |
| *C12N 15/113* | (2010.01) | |
| *A61K 38/48* | (2006.01) | |
| *A61K 39/00* | (2006.01) | |

(52) U.S. Cl.
CPC ...... *A61K 38/4813* (2013.01); *A61K 31/7105* (2013.01); *A61K 39/00* (2013.01); *A61K 39/3955* (2013.01); *C12N 15/1137* (2013.01); *C12N 2310/11* (2013.01); *C12N 2310/14* (2013.01); *C12N 2310/3231* (2013.01); *C12Y 304/11001* (2013.01)

(58) Field of Classification Search
CPC combination set(s) only.
See application file for complete search history.

(56) References Cited

U.S. PATENT DOCUMENTS

| | | |
|---|---|---|
| 5,856,487 A | 1/1999 | Upadhyay et al. |
| 2011/0027287 A1 | 2/2011 | Jackson et al. |
| 2011/0262386 A1 | 10/2011 | Bernhagen et al. |
| 2013/0195879 A1 | 8/2013 | Bylock |
| 2015/0140005 A1 | 5/2015 | Walley et al. |

FOREIGN PATENT DOCUMENTS

| | | |
|---|---|---|
| CN | 101467999 A | 7/2009 |
| CN | 101829113 A | 9/2010 |
| CN | 104815316 A | 8/2015 |
| CN | 107468687 A | 12/2017 |
| WO | WO-2011038149 A2 | 3/2011 |
| WO | WO-2017120222 A1 | 7/2017 |
| WO | WO-2018007999 A1 | 1/2018 |
| WO | WO-2019/236528 A1 | 12/2019 |

OTHER PUBLICATIONS

Farnier, "PCSK9 inhibitors," Curr Opin Lipidol 24:251-258 (2013) (Year: 2013).*
Pancreatitis, U.S. Department of Health and Human Services National Institutes of Health, NIH Publication No. 08-1596; pp. 1-8 (Jul. 2008) (Year: 2008).*
Shimada et al., "PCSK9 (Proprotein convertase subtilisin/kexin type 9) inhibitors: past, present, and the future," European Heart Journal 36:2415-2424 (2015) (Year: 2015).*
Schmid et al., "The role of infection in acute pancreatitis," Gut 45:311-316 (1999) (Year: 1999).*
Kloppel et al., "Pathology of Acute and Chronic Pancreatitis," Pancreas 8:659-670 (1993) (Year: 1993).*
Bergeron et al., "Proprotein Convertase Subtilisin/Kexin Type 9 Inhibition A New Therapeutic Mechanism for Reducing Cardiovascular Disease Risk," Circulation, 132:1648-1666 (2015).
Extended European Search Report for EP Application No. 19815628.3 dated Mar. 17, 2022.
International Search Report and Written Opinion for International Application No. PCT/US2019/035310 dated Sep. 8, 2019.
Kleef et al., "Chronic Pancreatits", Nature Reviews: Disease Primers, 3, 17060, 18 pages (2017).
Machicado et al., "Epidemiology of recurrent acute and chronic pancreatitis: Similarities and differences", Dig Dis Sci. 62(7): 1683-1691 (2017).
U.S. Appl. No. 14/399,157, Abandoned.
U.S. Appl. No. 17/854,808, Pending.
Abifadel et al., "Strategies for proprotein convertase subtilisin kexin 9 modulation: a perspective on recent patents," Expert Opin Ther Pat, 20(11):1547-1571 (2010).
Azzam et al., "Crosstalk between reverse cholesterol transport and innate immunity, Trends in Endocrinology and Metabolism," 23(4): 169-178 (2012).

(Continued)

*Primary Examiner* — Julie Ha
*Assistant Examiner* — Kristina M Hellman
(74) *Attorney, Agent, or Firm* — Foley Hoag LLP; David P. Halstead

(57) ABSTRACT

The present disclosure provides methods related to inhibiting or treating pancreatitis in a subject in need thereof, which include the use of a proprotein convertase subtilisin kexin 9 (PCSK9) inhibitor. The disclosed PCSK9 inhibitors and compositions including them can be used for treatment, inhibition, or prevention of pancreatitis in a subject. Treatment methods can include administering to the subject a therapeutically effective amount of a PCSK9 inhibitor.

6 Claims, No Drawings
Specification includes a Sequence Listing.

(56) References Cited

OTHER PUBLICATIONS

Banaszewska et al., "Proprotein convertase subtilisin/kexin type 9: A new target molecule for gene therapy," Cell Mol Biol Lett, 17(6):229-239 (2012).
Boekholdt et al., "Very Low Levels of Atherogenic Lipoproteins and the Risk for Cardiovascular Events: A Meta-Analysis of Statin Trials," J Am Coll Cardiol, 64(5):64(5):485-494 (2011).
Brautbar et al., "Pharmacological strategies for lowering LDL cholesterol: statins and beyond, Nat Rev Cardiol," 8:253-265 (2011).
Dias et al., "Effects of AMG 145 on Low-Density Lipoprotein Cholesterol Levels," 60(19):1888-1898 (2012).
Dong et al., "Inhibition of PCSK9 transcription by berberine involves down-regulation of hepatic HNF1a protein expression through the ubiquitin-proteasome degradation pathway," J Biol Chem., 290(7): pp. 4047-4058 (2015).
Duff et al., "PCSK9: an emerging target for treatment of hypercholesterolemia," Ex Opin Ther Tar, 15(2):157-168 (2011).
Extended European Search Report issued by the European Patent Office in corresponding Application No. 13791248.1 dated Sep. 21, 2015.
Fasolato et al., "PCSK9 Levels Are Raised in Chronic HCV Patients with Hepatocellular Carcinoma," Journal of Clinical Medicine, 9(3134): 10 pages (2020).
Frank-Kamenetsky et al., "Therapeutic RNAi targeting PCSK9 acutely lowers plasma cholesterol in rodents and LDL cholesterol in nonhuman primates." PNAS, 105(33):11915-11920 (2008).
Gormley et al., "Using genetic variants to evaluate the causal effect of cholesterol lowering on head and neck cancer risk: A Mendelian randomization study," PLOS Genetics, 17(4): 23 pages (2021).
Graham et al., "Antisense inhibition of proprotein convertase subtilisin/kexin type 9 reduces serum LDL in hyperlipidemic mice," J Lipid Res, 48:763-767 (2007).
Gumbiner et al., "Abstract 13322: The Effects of Single Dose Administration of RN316 (PF-04950615), a Humanized IgG2a Monoclonal Antibody Binding Proprotein Convertase Subtilisin Kexin Type 9, in Hypercholesterolemic Subjects Treated with and without Atorvastatin," Circulation, 126(21):A13322 (2012).
Guo et al., "PCSK9 Variants in Familial Hypercholesterolemia: A Comprehensive Synopsis," Frontiers in Genetics 11(1020): 13 pages (2020).
Gupta et al., "A Locked Nucleic Acid Antisense Oligonucleotide (LNA) Silences PCSK9 and Enhances LDLR Expression In Vitro and In Vivo," PLOS One, 5(5):e10682 (2010).
International Search Report and Written Opinion for International Application No. PCT/CA2013/000488 dated Sep. 10, 2013.

IUPHAR/BPS deposit of evolocumab, Guide to Pharmacology, [online], retrieved on Nov. 22, 2019. (https://www.guidetopharmnacology.org/GRAC/LigandDisplayForward?ligandId=7343).
Kui et al., "New Insights into the Methodology of L-Arginine-Induced Acute Pancreatitis," PLOS One, 10(2): 13 pages (2015).
Labonté et al., "PCSK9 Impeded Hepatitis C Virus Infection In Vitro and Modulates Liver CD81 Expression," Hepatology, vol. 50, No. 1, 17-24 (2009).
Levels et al., Distribution and Kinetics of Lipoprotein-Bound Endotoxin, Infect Immun, 69(5):2821-2828 (2001).
Levels et al., Distribution and Kinetics of Lipoprotein-Bound Lipoteichoic Acid, Infect Immun, 71(6):3280-3284 (2003).
Li et al., "Neutral sulfate berberine modulates cytokine secretion and increases survival in endotoxemic mice1," Acta PharmacolSin, 27(9):1199-1205 (2006).
Mahboobnia et al., "PCSK9 and cancer: Rethinking the link," Biomedicine and Pharmacotherapy, 140: 15 pages (2021).
Mbikay et al., "Of PCSK9, cholesterol homeostasis and parasitic infections: Possible survival benefits of loss-of-function PCSK9 genetic polymorphisms," Med Hypotheses, 69(5):1010-1017 (2007).
Ramanathan et al., "Alirocumab, a Therapeutic Human Antibody to PCSK9, Does Not Affect CD81 Levels or Hepatits C Virus Entry and Replication into Hepatocytes," PLOS One, 11(4): 14 pages (2016).
Standen et al., "Book Review: Septic Shock," N Engl J Med, 343:447-448 (2000).
Stein et al., "Effect of a Monoclonal Antibody to PCSK9 on LDL Cholesterol," N Engl J Med, 366:1108-1118 (2012).
Thain et al., "A low density lipoprotein (ldl) receptor modulator, Pcsk9, is associated with increased mortality in septic shock," Am J Resp Crit Care Med, 185:A5999 (2012).
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merck.com/mmpe/print/sec06/ch068/ch068a.html>. Sepsis and Septic Shock, see pp. 1-5.
Tingley et al., "Effects of a RG7652, a fully human mAb against proprotein convertase subtilisin/kexin type 9," Eur Heart J, 34:suppl 1 (2013).
Xiao et al., "Berberine inhibits dyslipidemia in C57BL/6 mice with lipopolysaccharide induced inflammation," Pharmacol Rep, 64(4):889-895 (2012).
Zhang et al., "Berberine Inhibits Cytosolic Phospholipase A2 and Protects Against LPS-Induced Lung Injury and Lethality Independent of The α2-Adrenergic Receptor in Mice," Shock, 29(5):617-622 (2008).

* cited by examiner

```
                       SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtctgtggaa gcg                                                          13
```

COMPOSITIONS AND METHODS FOR TREATING PANCREATITIS

RELATED APPLICATION

This application claims a right of priority from and the benefit of an earlier filing date of U.S. Provisional Application No. 62/680,896, filed Jun. 5, 2018, which is hereby incorporated by reference herein in its entirety.

SEQUENCE LISTING

The instant application contains a Sequence Listing, which has been submitted electronically in ASCII format and is hereby incorporated by reference in its entirety. Said ASCII copy, created on Apr. 6, 2022, is named AJH-00201_SL.txt and is 561 bytes in size.

BACKGROUND

Pancreatitis is inflammation of the pancreas, which can be either acute or chronic. Severe hypertriglyceridemia (triglycerides >1,000 mg/dL) can induce acute, life-threatening pancreatitis as triglyceride-rich lipoproteins infiltrate the pancreas, undergo lipolysis by pancreatic lipase, release toxic free fatty acids and trigger a cascade of inflammation. The severity and duration of a pancreatitis episode is generally proportional to the magnitude of hypertriglyceridemia, while the acute reduction of triglycerides is likely to improve the clinical course.

Currently available triglyceride-lowering agents, most of which are targeted to decreasing triglyceride synthesis, typically require weeks to months to lower triglycerides, and have no role in acute pancreatitis. There remains a need to identify a treatment that acutely lowers triglycerides, while decreasing the severity and duration of pancreatitis.

SUMMARY OF THE INVENTION

In certain aspects, the present disclosure provides methods for inhibiting or treating pancreatitis, especially acute pancreatitis, in a subject in need thereof, comprising administering a therapeutically effective amount of a PCSK9 inhibitor to the subject. In certain aspects, the present disclosure provides PCSK9 inhibitors for treating pancreatitis.

In an aspect, use of a proprotein convertase subtilisin kexin 9 (PCSK9) inhibitor in manufacture of a medicament for treatment, inhibition, or prevention of pancreatitis in a subject in need thereof is disclosed. In another aspect, a method of producing a pharmaceutical composition for treating, inhibiting, or preventing pancreatitis is disclosed, e.g., by mixing a PCSK9 inhibitor with at least one substance, such as a carrier or excipient, to form the pharmaceutical composition. In another aspect, a pharmaceutical composition comprising a PCSK9 inhibitor for use in treatment, inhibition, or prevention of pancreatitis is disclosed. In yet another aspect, a PCSK9 inhibitor for use in treatment, inhibition, or prevention of pancreatitis is disclosed. In one aspect, a method of treating, inhibiting, or preventing pancreatitis in a non-human subject in need thereof is disclosed, which method includes administering to the subject a PCSK9 inhibitor, e.g., thereby reducing symptoms of the pancreatitis. In an aspect, use of a PCSK9 inhibitor for treatment, inhibition, or prevention of pancreatitis is disclosed. In some aspects, a method of treating, inhibiting, or preventing pancreatitis in a subject in need thereof is disclosed, which method includes administering to the subject a PCSK9 inhibitor, e.g., thereby reducing one or more symptoms of the pancreatitis. In another aspect, a method of treating, inhibiting, or preventing pancreatitis in a subject in need thereof is disclosed, which includes administering to the subject a pharmaceutical composition comprising a PCSK9 inhibitor.

Each of these aspects has various embodiments. For example, the pancreatitis can be acute pancreatitis or chronic pancreatitis; the PCSK9 inhibitor can be a monoclonal antibody or antigen-binding fragment thereof (e.g., AMG145 (Evolocumab), 1D05-IgG2, SAR236553/REGN727 (Alirocumab), RN-316 (Bococizumab), LGT209, LY3015014 (Frovocimab), RG7652); the PCSK9 inhibitor can be a peptide mimetic (e.g., an EGFA domain mimic, EGF-A peptide, a fibronectin based scaffold domain protein, a neutralizing PCSK9 variant); the PCSK9 inhibitor can be an antisense oligonucleotide (e.g., BMS-PCSK9Rx); the PCSK9 inhibitor can be an RNAi molecule (e.g., LNA ASO, ALN-PCS). The subject, in some embodiments, is a human.

DETAILED DESCRIPTION OF THE INVENTION

Low density lipoprotein (LDL) receptors remove cholesterol-rich LDL particles from the bloodstream by binding apoB100 and facilitating particle endocytosis. Proprotein convertase subtilisin kexin 9 (PCSK9) is a key regulator of LDL receptors that prevents the recycling of these receptors back to the cell surface, resulting in less efficient LDL particle uptake. Inhibition of PCSK9 has been shown to increase levels of cell surface LDL receptors, resulting in a substantial decrease in low-density lipoprotein cholesterol (LDL-C) levels. Recent clinical data has shown that the reduction of LDL-C induced by PCSK9 inhibition is associated with an improvement in cardiovascular outcomes.

LDL receptors also play a key role in the removal of triglyceride-rich lipoproteins (e.g., very low-density lipoproteins (VLDL) and chylomicron remnants) from the bloodstream by binding apoE and facilitating particle endocytosis. PCSK9 appears to play an important role in metabolism of remnant lipoproteins, just as it does for LDL metabolism. In both mice and humans, a genetic loss of function of PCSK9 is associated with a reduction in postprandial triglyceride levels, which appears to be mediated primarily by an increase in clearance of triglyceride-rich lipoprotein remnants. Therefore, it is likely that pharmacological inhibition of PCSK9 would lead to an increased clearance of triglyceride-rich lipoproteins.

Pharmacological PCSK9 inhibition increases LDL receptor expression, effectively scavenging triglyceride-rich remnant lipoproteins. When given in the setting of triglyceride-induced pancreatitis, PCSK9 inhibition lowers triglycerides, decreases the severity and duration of pancreatitis, and benefits the clinical course of the patient with decreased hospitalization duration, morbidity and mortality.

In certain aspects, the present disclosure provides methods for inhibiting or treating pancreatitis in a subject in need thereof, comprising administering a PCSK9 inhibitor to the subject. In some embodiments, the pancreatitis is acute pancreatitis or chronic pancreatitis, preferably acute pancreatitis.

In certain aspects, the present disclosure also provides PCSK9 inhibitors for treating pancreatitis.

In some embodiments, the PCSK9 inhibitor is an antibody or antigen-binding fragment thereof, such as a monoclonal antibody or antigen-binding fragment thereof. For example, the PCSK9 inhibitor can be AMG145 (Evolocumab), 1D05-IgG2, SAR236553/REGN727 (Alirocumab), RN-316 (Bococizumab), LGT209, LY3015014 (Frovocimab), or RG7652. In other embodiments, the PCSK9 inhibitor is a peptide mimetic, such as an EGFA domain mimic, EGF-A peptide, a fibronectin based scaffold domain protein, or a neutralizing PCSK9 variant.

The PCSK9 inhibitor may be an antisense oligonucleotide, such as BMS-PCSK9Rx. Alternatively, the PCSK9 inhibitor may be an RNAi molecule, such as LNA ASO or ALN-PCS.

In certain preferred embodiments, the subject is human.

Pancreatitis

Pancreatitis is inflammation of the pancreas. The pancreas, located under the stomach in the retroperitoneum, secretes digestive enzymes necessary for the digestion and absorption of food, and also secretes hormones to regulate metabolism. Pancreatitis, which can be divided into acute pancreatitis and chronic pancreatitis, is developed when autolysis of the pancreas is induced by digestive enzymes (e.g., amylase, trypsin, and lipase).

The most common causes of acute pancreatitis are gallstones and heavy alcohol use. Other causes include direct trauma, certain medications, infections such as mumps, and tumors. Chronic pancreatitis may develop as a result of acute pancreatitis, but is most commonly due to many years of heavy alcohol use. Other causes include high levels of blood fats (triglycerides), high blood calcium, some medications, and certain genetic disorders such as cystic fibrosis. Smoking increases the risk of both acute and chronic pancreatitis. Diagnosis of acute pancreatitis is based on a threefold increase in the blood of either amylase or lipase. In chronic pancreatitis these tests may be normal.

Pancreatitis causes damage to pancreatic acinar cells, extensive interstitial edema, hemorrhage, and migration of neutrophilic granulocytes to the site of injury. Approximately 20% of pancreatitis patients undergo a severe clinical course involving multiple organ failure and systemic complications such as pancreatic necrosis and injury. Additionally, there is a 10% fatality rate of patients hospitalized with acute pancreatitis.

Early complications of pancreatitis include shock, infection, systemic inflammatory response syndrome, low blood calcium, high blood glucose, and dehydration. Blood loss, dehydration, and fluid leaking into the abdominal cavity (ascites) can lead to kidney failure. Respiratory complications are often severe. Pleural effusion is usually present. Shallow breathing from pain can lead to lung collapse. Pancreatic enzymes may attack the lungs, causing inflammation. Severe inflammation can lead to intraabdominal hypertension and abdominal compartment syndrome, further impairing renal and respiratory function and potentially requiring management with an open abdomen to relieve the pressure.

Late complications include recurrent pancreatitis and the development of pancreatic pseudocysts, collections of pancreatic secretions that have been walled off by scar tissue. These may cause pain, become infected, rupture and bleed, block the bile duct and cause jaundice, or migrate around the abdomen. Acute necrotizing pancreatitis can lead to a pancreatic abscess, a collection of pus caused by necrosis, liquefaction, and infection. This happens in approximately 3% of cases, or almost 60% of cases involving more than two pseudocysts and gas in the pancreas.

Current treatment of pancreatitis depends on the severity of the inflammation, and is largely supportive and aimed at decreasing the pain caused by the disease. Severe acute pancreatitis has mortality rates around 2-9%, which is higher where necrosis of the pancreas has occurred.

PCSK9 and PCSK9 Inhibitors

PCSK9 is a secreted protein expressed primarily in the liver and small intestine. It is the ninth member of the family of proprotein convertases (PC). PCSK9 differs from the other PC in that is has only itself as a substrate and it escorts the low density lipoprotein receptor (LDLR) to the lysosome for degradation.

The PCSK9 gene encodes a proprotein, which has also been termed Narc 1, a proteinase that is related to proteinase K. PCSK9 is synthesized as a 74 kDa proprotein that undergoes cleavage in the endoplasmic reticulum resulting in secretion of a ~14 kDa fragment and a ~60 kDa fragment held together by non-covalent bonds. Further auto-catalytic cleavage of the ~14 kDa fragment produces the active PCSK9. The active PCSK9 protein circulating in the plasma binds the LDL receptor and, after internalization, prevents recycling of the receptor back to the cell surface and promotes degradation of the receptor in the lysosome.

Exemplary PCSK9 inhibitors are described below.

Monoclonal Antibodies

Monoclonal antibodies (mAbs) that specifically bind to PCSK9 are capable of inhibiting PCSK9 activity. In some instances, the mAbs bind near the catalytic domain, which interacts with the low density lipoprotein receptor (LDLR) thereby inhibiting the catalytic activity of PCSK9 on LDLR. A number of these mAbs are in clinical trials (for example, AMG145/Evolocumab (Amgen), 1D05-IgG2 (Merck & Co.), and SAR236553/REGN727/Alirocumab (Aventis/Regeneron)). Similarly, additional mAbs targeting PCSK9 are also in development (for example, RN-316/Bococizumab (Pfizer), LGT209 (Novartis), LY3015014/Frovocimab (Eli Lilly), RG7652 (Roche/Genentech)). A number of PCSK9 inhibitory antibodies and fragments thereof are described in the patent literature as follows: Merck/Schering Corp. (PCT/US2008/081311), Schering Corp. (PCT/US2011/056649), Regeneron Pharmaceuticals, Inc. (PCT/US2012/054756, PCT/US2012/048574, PCT/US2009/068013), Sanofi (PCT/EP2012/051318, PCT/EP2012/051320, PCT/EP2012/051321), Eli Lilly and Company (PCT/US2012/054737), Affiris Ag (PCT/EP2012/067950), Pfizer (PCT/IB2012/053534, PCT/IB2012/050924, PCT/IB2010/053784), Novartis AG (PCT/EP2012/061045, PCT/US2012/041214, PCT/EP2008/054417), IRM LLC and Novartis AG (PCT/US2012/024633, PCT/US2010/059959), Genentech Inc. and Hoffmann La Roche (PCT/US2011/024633), Merck Sharp & Dohme (PCT/US2010/054714, PCT/US2010/054640, PCT/US2010/048849), Rinat Neuroscience Corp/Pfizer (PCT/IB2009/053990), Merck & Co Inc. (PCT/US2009/033369, PCT/US2009/033341, PCT/US2007/02322, PCT/US2007/023213, PCT/US2007/023212, PCT/US2007/023169), and Amgen Inc. (PCT/US2008/074097).

PCSK9-mediated activity on cell surface LDLRs has been reversed using antibodies that recognize epitopes on PCSK9. In particular, where those epitopes are associated with the catalytic domain. Intravenous infusion of an Amgen monoclonal antibody (AMG145) specific for the catalytic domain of PCSK9 resulted in a significant reduction of circulating LDL-C levels as early as 8 hours after injection in non-human primates. Merck & Co.'s monoclonal antibody (1D05-IgG2) structurally mimics the EGFA domain of the LDLR. A single injection of 1D05-IgG2 was also found to antagonize PCSK9 function in non-human primates, resulting in reduced plasma LDL-C levels by up to 50%. Pfizer-Rinat and Sanofi-Aventis/Regeneron also have monoclonal antibodies (RN316 and SAR236553/REGN727, respectively) in clinical trials.

Peptides

Peptides that mimic the EGFA domain of the LDLR that binds to PCSK9 have been developed to inhibit PCSK9. Similarly, EGF-A peptides, fibronectin based scaffold domain proteins, which bind PCSK9, and neutralizing PCSK9 variants (for example, with a Pro/Cat domain), have been developed, all of which have been shown to inhibit PCSK9 activity.

A number of PCSK9 inhibitory peptides are described in the patent literature as follows: Schering Corp. (PCT/US2009/044883), Genentech Inc. and Hoffmann La Roche (PCT/US2012/043315), Squibb Bristol Myers Co. (PCT/US2011/032231, PCT/US2007/015298), Angeletti P Ist Richerche Bio (PCT/EP2011/054646), and Amgen Inc. (PCT/US2009/034775).

Oligonucleotides

A PCSK9 antisense oligonucleotide from Isis Pharmaceuticals/Bristol-Myers Squibb (BMS-PCSK9Rx) has been shown to increase expression of the LDLR and decrease circulating total cholesterol levels in mice. Similarly, a locked nucleic acid from Santaris Pharma (LNA ASO) reduced PCSK9 mRNA levels in mice. LNA ASO, complementary to the human and mouse PCSK9 mRNA (accession nos. NM174936 and NM153565), is a 13-nucleotide long gapmer with the following sequence: GTctgtggaaGCG (SEQ ID NO: 1) (uppercase LNA, lowercase DNA) and phosphorothioate internucleoside linkages.

Alnylam Pharmaceuticals has shown positive results in clinical trials for a siRNA (ALN-PCS) for the inhibition of PCSK9. The siRNA was incorporated into lipidoid nanoparticles to minimize toxicity and intravenously infused in rats, mice, and monkeys, resulting in reduced LDL-C levels after administration.

A number of PCSK9 inhibitory oligonucleotides are described in the patent literature as follows: Santaris Pharma A/S (PCT/EP2007/060703, PCT/EP2009/054499, PCT/EP2010/059257), Isis Pharmaceutical Inc. (PCT/US2007/068404), siRNA Therapeutics Inc. (PCT/US2007/073723), Alnylam Pharmaceuticals Inc. (PCT/US2011/058682, PCT/US2010/047726, PCT/US2010/038707, PCT/US2009/032743, PCT/US2007/068655), RXi Pharmaceuticals Corp. (PCT/US2010/000019), Intradigm Corp. (PCT/US2009/036550), and Nastech Pharm Co. (PCT/US2008/055554).

Small Molecules

Serometrix has reported a small molecule inhibitor of PCSK9 (SX-PCSK9). Similarly, berberine may be used as a PCSK9 inhibitor.

These patents and publications are incorporated by reference herein in their entireties, and in particular for their disclosure of PCSK9 inhibitors.

The methods and compositions of the present disclosure relate to the use of a PCSK9 inhibitor. The PCSK9 inhibitor useful in the compositions disclosed herein may be any suitable PCSK9 inhibitor.

DEFINITIONS

As used herein the specification, "a" or "an" may mean one or more. As used herein in the claim(s), when used in conjunction with the word "comprising", the words "a" or "an" may mean one or more than one. As used herein "another" may mean at least a second or more.

The terms "administration" and/or "administering" should be understood to mean providing a compound or a prodrug of a compound to a subject in need of treatment.

As used herein, "monoclonal antibody" or "mAb" refers to an antibody from a population of substantially homogeneous antibodies (i.e., where the individual antibodies are identical to one another, with the possible exception of some naturally-occurring mutations). MAbs are highly specific, being directed against a single antigenic site and are often directed against a single determinant on an antigen.

As used herein, "humanized" antibody is meant to refer to forms of non-human (e.g., murine) antibodies that are chimeric immunoglobulins, immunoglobulin chains, or fragments thereof (such as Fv, Fab, Fab', F(ab')2, or other antigen-binding subsequences of antibodies) that contain minimal sequences derived from non-human immunoglobulin. Many humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

The phrase "pharmaceutically-acceptable carrier" as used herein means a pharmaceutically-acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein "RNAi" is meant to include any of the gene silencing methods known in the art, including post-transcriptional gene silencing (PTGS) methods. These may include, but are not limited to any one or more of the following: microRNA (miRNA), small interfering RNA (siRNA), short hairpin RNA (shRNA), primary-microRNA (pri-miRNA), asymmetric interfering RNA (aiRNA), small internally segmented RNA (sisiRNA), meroduplex RNA (mdRNA), RNA-DNA chimeric duplex, trans-kingdom RNA (tkRNA), tRNA-shRNA, tandem siRNA (tsiRNA), tandem hairpin RNA (thRNA), pri-miRNA mimic cluster, and transcriptional gene silencing (TGS).

The term "subject" refers to a mammal, including, but not limited to, a human or non-human mammal, such as a bovine, equine, canine, ovine, or feline.

As used herein, the term "treating" or "treatment" includes reversing, reducing, or arresting the symptoms, clinical signs, and underlying pathology of a condition in a manner to improve or stabilize a subject's condition.

The term "therapeutic treatment" is art-recognized and includes administering to the subject a composition after the manifestation of an unwanted condition, such as pancreatitis.

The term "substance" includes all ingredients that can be included in a pharmaceutical composition (e.g., water, other solvents, carriers, excipients).

Therapeutic Methods

Provided herein are methods of inhibiting or treating pancreatitis in a subject in need thereof, comprising administering a proprotein convertase subtilisin kexin 9 (PCSK9) inhibitor to the subject. In some embodiments, the methods relate to treating pancreatitis, e.g., acute pancreatitis or chronic pancreatitis. Also provided are methods of treating pancreatitis in a subject in need thereof, comprising administering to the subject a therapeutically effective amount of a pharmaceutical composition comprising a PCSK9 inhibitor as disclosed herein.

Compositions

In some aspects, the invention relates to a pharmaceutical composition comprising a PCSK9 inhibitor for treating pancreatitis. The composition may comprise a pharmaceutically acceptable carrier. The pharmaceutical compositions disclosed herein may be delivered by any suitable route of administration, including orally, buccally, sublingually, parenterally, and rectally, as by powders, ointments, drops, liquids, gels, tablets, capsules, pills, or creams. In certain embodiments, the pharmaceutical compositions are delivered systemically (e.g., via oral administration). In some embodiments, the compositions disclosed herein are delivered intravenously.

Actual dosage levels of the active ingredients in the pharmaceutical compositions may be varied so as to obtain an amount of the active ingredient which is effective to achieve the desired therapeutic response for a subject, composition, and mode of administration, without being toxic to the subject.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required to achieve the desired therapeutic effect and gradually increase the dosage until the desired effect is achieved.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of treating acute pancreatitis or chronic pancreatitis in a subject in need thereof, the method comprising administering to the subject a proprotein convertase subtilisin kexin 9 (PCSK9) inhibitor, wherein the acute pancreatitis is not caused by an infection,
   wherein the PCSK9 inhibitor is AMG145 (Evolocumab), 1D05-IgG2, SAR236553/REGN727 (Alirocumab), RN-316 (Bococizumab), LGT209, LY3015014 (Frovocimab), or RG7652.

2. The method of claim 1, wherein the method treats acute pancreatitis.

3. The method of claim 1, wherein the subject is human.

4. A method of treating acute pancreatitis or chronic pancreatitis in a subject in need thereof, the method comprising administering to the subject a pharmaceutical composition comprising a proprotein convertase subtilisin kexin 9 (PCSK9) inhibitor, wherein the acute pancreatitis is not caused by an infection,
   wherein the PCSK9 inhibitor is AMG145 (Evolocumab), 1D05-IgG2, SAR236553/REGN727 (Alirocumab), RN-316 (Bococizumab), LGT209, LY3015014 (Frovocimab), or RG7652.

5. The method of claim 4, wherein the method treats acute pancreatitis.

6. The method of claim 4, wherein the subject is human.

* * * * *